(12) United States Patent
Bologna et al.

(10) Patent No.: US 6,624,200 B2
(45) Date of Patent: Sep. 23, 2003

(54) BIOADHESIVE PROGRESSIVE HYDRATION TABLETS

(75) Inventors: William J. Bologna, Paris (FR); Howard L. Levine, Oceanside, NY (US); Dominque DeZiegler, Paris (FR)

(73) Assignee: Columbia Laboratories, Inc., Livingston, NJ (US)

( * ) Notice: Subject to any disclaimer, the term of this patent is extended or adjusted under 35 U.S.C. 154(b) by 34 days.

(21) Appl. No.: 09/877,218

(22) Filed: Jun. 11, 2001

(65) Prior Publication Data

US 2002/0044964 A1 Apr. 18, 2002

Related U.S. Application Data

(63) Continuation-in-part of application No. 09/596,073, filed on Jun. 16, 2000, which is a continuation-in-part of application No. 08/379,310, filed on Aug. 23, 1999, now Pat. No. 6,248,358.
(60) Provisional application No. 60/097,843, filed on Aug. 25, 1998.

(51) Int. Cl.$^7$ ........................ A01N 33/02; A61K 31/135
(52) U.S. Cl. ................................... 514/653; 514/649
(58) Field of Search ................... 424/465; 514/649, 514/653

(56) References Cited

U.S. PATENT DOCUMENTS

| | | | |
|---|---|---|---|
| 3,133,862 A | 5/1964 | Wershaw et al. | |
| 4,226,848 A | 10/1980 | Nagai et al. | |
| 4,389,393 A | 6/1983 | Schor et al. | |
| 4,540,566 A | 9/1985 | Davis et al. | |
| 4,572,832 A | 2/1986 | Kigasawa et al. | |
| 4,596,795 A | 6/1986 | Pitha | |
| 4,615,697 A | 10/1986 | Robinson | |
| 4,740,365 A | 4/1988 | Yukimatsu et al. | |
| 4,764,378 A | 8/1988 | Keith et al. | |
| 4,900,552 A | 2/1990 | Sanvordeker et al. | |
| 4,915,948 A | 4/1990 | Gallopo et al. | |
| 5,102,666 A | 4/1992 | Acharya | |
| 5,110,605 A | 5/1992 | Acharya | |
| 5,252,334 A | 10/1993 | Chiang et al. | |
| 5,298,017 A | 3/1994 | Theeuwes et al. | |
| 5,362,498 A | 11/1994 | Aiache | |
| 5,458,884 A | 10/1995 | Britton et al. | |
| 5,460,820 A | 10/1995 | Ebert et al. | |
| 5,554,380 A | 9/1996 | Cuca et al. | |
| 5,624,677 A | 4/1997 | El-Rashidy et al. | |
| 5,650,192 A | 7/1997 | Britton et al. | |
| 5,656,284 A | 8/1997 | Balkin | |
| 5,686,094 A | 11/1997 | Acharya | |
| 5,750,134 A | 5/1998 | Scholz et al. | |
| 5,750,136 A | 5/1998 | Scholz et al. | |
| 5,766,620 A | 6/1998 | Heiber et al. | |
| 5,780,045 A | 7/1998 | McQuinn et al. | |
| 5,783,208 A | 7/1998 | Venkateshwaran et al. | |
| 5,783,212 A | 7/1998 | Fassihi et al. | |
| 5,800,832 A | 9/1998 | Tapolsky et al. | |
| 5,804,209 A | 9/1998 | De Ponti et al. | |
| 5,807,575 A | 9/1998 | Dumoulin et al. | |
| 5,853,762 A | 12/1998 | Myers et al. | |
| 5,855,905 A | 1/1999 | Oettel et al. | |
| 5,958,458 A | 9/1999 | Norling et al. | |
| 6,017,521 A | 1/2000 | Robinson et al. | |
| 6,063,404 A | * 5/2000 | Timpe et al. | ............... 424/464 |
| 6,242,495 B1 | 6/2001 | Leone-Bay et al. | |

FOREIGN PATENT DOCUMENTS

| | | |
|---|---|---|
| EP | 0 159 604 A2 | 10/1985 |
| EP | 0 273 209 B1 | 1/1992 |
| EP | 0 488 139 A1 | 6/1992 |
| EP | 0 654 261 A1 | 5/1995 |
| EP | 0 770 384 A1 | 5/1997 |
| JP | 06-100466 | 4/1994 |
| WO | WO 00/76522 A1 | 12/2000 |

OTHER PUBLICATIONS

Voorspoels et al., "Buccal Absorption of Testosterone and its Esters Using a Bioadhesive Tablet in Dogs," *Pharmaceutical Research*, vol. 13, No. 8, 1996; pp. 1228–1232.
Kim et al., *Contraception*, 1995, 52, pp. 314–316.
Dobs et al., *JCE&M* 1998, vol. 83, No. 1, pp. 34–39.
Pitha et al., "Hydrophilic Cyclodextrin Derivatives Enable Effective Oral Administration of Steroidal Hormones," *Journal of Pharmaceutical Sciences*, vol. 75, No. 2, Feb. 1986, pp. 165 and 167.
Conway et al., "Randomized clinical trial of testosterone replacement therapy in hypogonadal men," *Int'l J. of Andrology*, 1988, 11, pp. 247–264.

* cited by examiner

Primary Examiner—Alton N. Pryor
(74) Attorney, Agent, or Firm—Winston & Strawn

(57) ABSTRACT

A bioadhesive composition wherein the active ingredient may be protected from water or the surrounding environment, thereby protecting it from metabolism or from other degradation caused by moisture, enzymes, or pH effects, and making it bioavailable only at a controlled rate. The active ingredient may be protected from moisture during the manufacturing process and more importantly may be protected from moisture and the immediate septic environment until after the patient has applied the composition, and then only at a slow and controlled rate. It is by this process of progressive hydration that the active ingredient remains protected for many hours after administration. It is also by the process of progressive hydration that controlled and sustained release is achieved because only that part of the active ingredient that is the hydrated (aqueous) fraction of the composition is available for absorption (bioavailable).

13 Claims, 6 Drawing Sheets

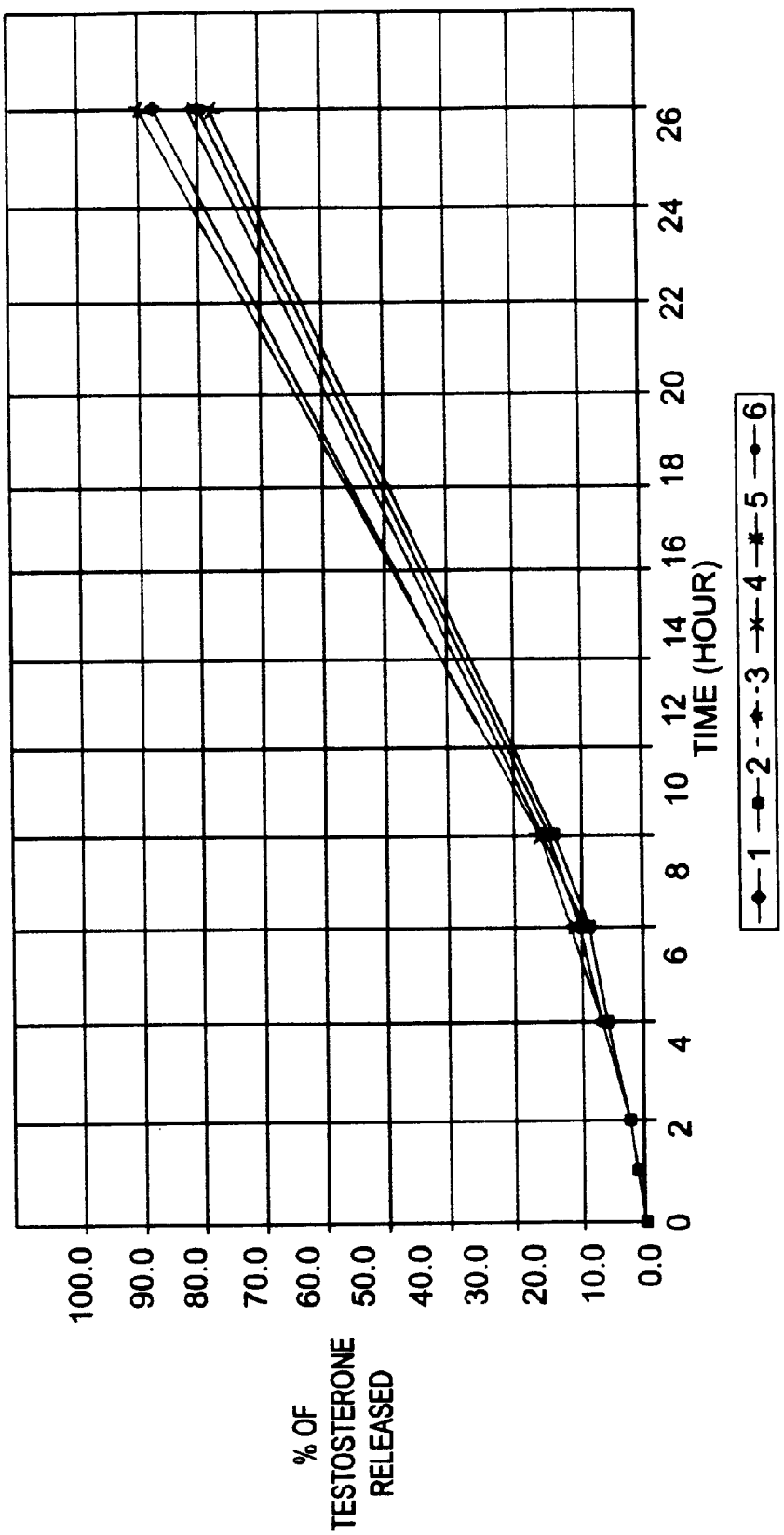

BIOADHESIVE PROGRESSIVE HYDRATION TABLETS

This is a continuation-in-part of application Ser. No. 09/596,073, filed Jun. 16, 2000, which is a continuation-in-part of U.S. application Ser. No. 09/379,310, filed Aug. 23, 1999, now U.S. Pat. No. 6,234,358 which claims the benefit of provisional application Ser. No. 60/097,843, filed Aug. 25, 1998.

The present invention relates to bioadhesive, bioerodible compositions for the extended and controlled release of active ingredients. More particularly, the present invention relates to progressive hydration tablets for adhesion to the wall of a body cavity for the sustained release of active ingredients without premature degradation of the active ingredients caused by metabolism, or by moisture, enzymes or pH effects.

Medications and other pharmaceutical products have traditionally been administered in doses via oral ingestion, nasal sprays or injections. These delivery methods have proven ineffective for patients needing a prolonged and constant supply of an active ingredient delivered to the bloodstream. Particularly difficult are patients needing dosing during sleep time hours. For these patients, intravenous ("IV") lines, slow-dissolving pills, and suppositories or transdermal patches have been prescribed. However, the inconvenience and discomfort of IVs, the short life span of many ingested active ingredients from gastrointestinal degradation or first-pass liver metabolism, and the inability of many products to be comfortably delivered transdermally in suitable doses or in controlled concentrations have proven these methods unsatisfactory.

Previous artisans have attempted to meet the needs of the art by developing products for the transmucosal administration of active ingredients. For example, certain active ingredients can be administered quickly into the bloodstream via the walls of a body cavity, such as the buccal or vaginal cavities, without the risk of first pass hepatic degradation. Generally, delivery of active ingredients through mucosal surfaces may be enhanced by the use of bioadhesive formulations. However, one particular area where those in the art have attempted, but heretofore failed, to meet the needs of the art is in developing a bioadhesive tablet useful for sustained release applications without risking degradation of the active ingredient before it is actually released.

"Sustained release" generally refers to continuous or sporadic release of an active ingredient over an extended time after a single administration, whereby the level of active ingredient available to the host patient often is maintained at some constant level over a period of time. As used herein, it is also intended to cover the situation where the release of an active ingredient is controlled over a period of time wherein the level of active ingredient available to the host (bioavailability) may be at a variable but predetermined level at a particular instant in time of treatment.

The sustained release bioadhesive tablets known in the art can be generally broken down into two categories: (1) tablets consisting of water soluble carbomers, and (2) tablets consisting of insoluble polymers. Both types of tablets have proven unsatisfactory for many applications. For example, numerous artisans have attempted to formulate a suitable sustained release bioadhesive tablet from water soluble carbomers, such as carbomer 934P or CARBOPOL™ 974 resin (commercially available from B. F. Goodrich, Cleveland, Ohio). However, such tablets often are only able to adhere to the wall of a body cavity for short periods of time, e.g., six hours or less. Also, these tablets are easily dislodged from the wall of a body cavity and thus place patients using such tablets buccally at risk of asphyxiation. Furthermore, these prior art tablets inherently become hydrated relatively quickly and thus may prematurely expose the reservoir of active ingredient to degradation by moisture or by enzymes from the host environment such as from bacteria in the septic oral or vaginal cavities.

Similarly, tablets comprised of insoluble polymers, such as Polycarbophil, have proven unsuitable for many applications. For example, although Polycarbophil tablets are capable of prolonged attachment to the wall of a body cavity, such tablets do not adhere immediately, making them impractical for certain treatments such a buccal delivery of active ingredients to patients during sleep time hours. Further, such tablets often do not soften sufficiently to provide comfort and imperceptibility, or provide safety from potential aspiration of the tablet.

Furthermore, for example, neither type of prior art tablet is particularly suitable for treating many conditions. As alluded to previously, there are numerous medical conditions in which a sustained and/or controlled release of active ingredient(s) is desired for any of numerous reasons including, for example, to alleviate the impact of first-pass hepatic metabolism of the active ingredient or the risk of premature degradation of the active ingredient by moisture, pH effects, or enzymes, or to attain the comfort and convenience offered by a suitable bioadhesive tablet. Such conditions include, but are not limited to, for example, those needing treatment with an active ingredient that may be, but is not limited to, a glycoprotein, protein, sex hormone, anti-hormone, nitrate, beta-agonist, beta-antagonist, opioid, opioid-antagonist, antidepressant, HMG CoA (3-hydroxy-3-methylglutaryl Coenzyme A) reductase inhibitor, antihistamine, ACE (angiotensin converting enzyme) inhibitor, and/or prostaglandin. Heretofore the art has required such patients to undergo the more invasive and less suitable techniques and methods of delivery described above.

To illustrate the need in the art, consider hypogonadal men, for example. Hypogonadism in man is characterized by a deficiency or absence of endogenous testosterone production. Abnormally low levels of testosterone may place men at risk of "Andropause", wherein men are at greater risk of cardiovascular disease, Alzheimer's disease, and osteoporosis.

Testosterone has traditionally been used to treat hypogonadal men. However, to be most effective, the treatment must be capable of complete physiologic testosterone replacement. Moreover, the treatment must be capable of providing sustained levels of testosterone through the night, preferably sustaining a peak in the middle of the night. Transdermal testosterone patches typically produce only sub-physiologic levels and thus incomplete relief. Similarly, the prior art buccal tablets heretofore described would be ineffective or impractical for such sustained testosterone delivery.

The hormone testosterone, like many other drugs, including many other proteins and glycoproteins, undergoes high first pass metabolism. Accordingly, as will be appreciated by one of ordinary skill in the art, buccal or vaginal tablets consisting of materials that are incapable of keeping the interior reservoir of the tablet in the dry state for prolonged periods are inherently incapable of preventing dissolution and swallowing or dissolution and rapid absorption of the active ingredient through the mucosa. Furthermore, as will be appreciated by one of ordinary skill in the art, tablets which are unable to quickly adhere to the target area or are able to become dislodged are impractical for treatments which use night-time delivery, such as testosterone treatment.

Active ingredients such as testosterone may also undergo undesired metabolism. For example, 5α-reductase converts testosterone to 5α-dihydrotesterone (DHT). DHT may cause adverse effects such as hair loss and prostate disorders. Similarly, 5α-reductase may metabolize other active ingredients such as progesterone.

Various testosterone formulations have been developed to circumvent the problems inherent in rapid clearance of orally and parenterally administered agents. These include transdermal preparations (with or without emollient), pellets for subcutaneous implantation, biodegradable microcapsule formulations for injection, and inclusion complexes that enhance sublingual absorption of the hormone. Of these, the testosterone transdermal system for use on the scrotum and other skin patch products, are probably the most widely tested. Under optimal conditions, they are intended to approximate the physiological pattern of hormone levels throughout the day and provide an alternative to parenteral therapy.

However, the scrotal preparation causes a disproportionate increase in plasma dihydrotestosterone (DHT) to a level that is 30 to 40% that of testosterone, presumably because of the high level of 5α-reductase in scrotal skin. Other skin patches likewise produce high levels of DHT. Such increases in serum DHT have also been reported after treatment with the extremely long-acting parenteral testosterone ester testosterone buciclate and with the oral ester testosterone undecanoate. Williams Textbook of Endocrinology, $9^{th}$ Ed., W. B. Saunders Company, p. 853. Thus, the present invention advantageously avoids the side effects that may be caused by 5α-reductase's metabolism of active ingredients.

Furthermore, as will be appreciated by one of ordinary skill in the art, the advantages of a sustained release, bioadhesive tablet according to the present invention are not limited to the treatment of hypogonadism in men. For example, patients often require sustained release hormone treatment for various conditions. In addition, other medications, such as steroids for treating such conditions as asthma, involve treatments where desired peak levels are at night during sleep-time hours. Accordingly, one of ordinary skill in the art will appreciate that there exists a long-felt, yet unresolved, need to develop a bioadhesive, sustained release tablet to overcome the aforementioned needs of the art, including, but not limited to, the delivery of therapeutically effective amounts of an active ingredient which may be metabolized or otherwise degraded by moisture, enzymes, or pH effects, such as glycoproteins, proteins, sex hormones, anti-hormones, nitrates, beta-agonists, beta-antagonists, opioids, opioid-antagonists antidepressants, HMG CoA reductase inhibitors, antihistamines, ACE inhibitors, and/or prostaglandins.

For example, an advantage to administering treating agents such as terbutaline (especially for sleep time administration) through a sustained release bioadhesive tablet according to the instant invention is that such administration provides controlled, extended release to help prevent high peak blood serum levels of the terbutaline. This is particularly useful when the treating agent, such as terbutaline, is associated with adverse side effects at high blood serum levels.

BRIEF DESCRIPTION OF THE DRAWINGS

FIGS. 3 through 6 depict the testosterone release rate for four different progressive hydration formulations, as discussed further below.

SUMMARY OF THE INVENTION

Figure 1:
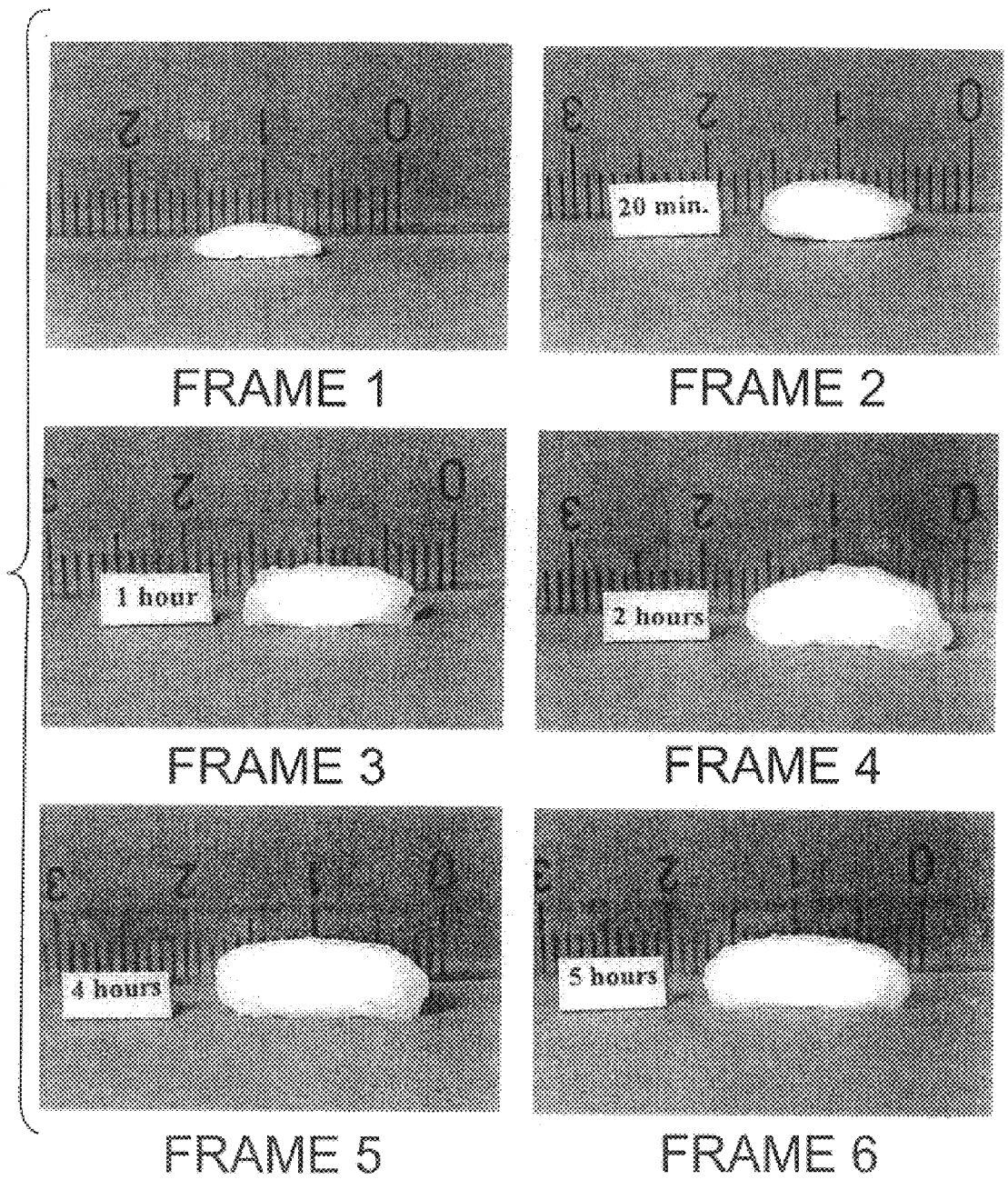
FIG. 1 is a series of photographs depicting the progressive hydration of a bioadhesive tablet according to the invention.

The present invention meets the aforementioned needs in the art. Accordingly, it is an object of the invention to provide a bioadhesive tablet that adheres immediately or almost immediately to the target tissue area of a body cavity and generally stays attached substantially throughout treatment. In accordance with this aspect of the invention, there is provided a bioadhesive tablet that can stay attached and deliver active ingredients in the buccal cavity for as much as eighteen hours or more. In accordance with a related aspect of the invention, there is provided a bioadhesive tablet that can stay attached and deliver active ingredients vaginally for as much as 72 hours or more.

It is another object of the invention to provide a bioadhesive tablet that progressively hydrates, whereby the inner core of the tablet remains protected from moisture and the surrounding environment. In accordance with this aspect of the invention there is provided a bioadhesive tablet suitable for sustained release use in mucosal and other body cavities even with active ingredients comprising proteins or glycoproteins or other treating agents that are particularly susceptible to metabolism, or to enzymatic, pH, or moisture-induced degradation.

It is a related object of the invention to provide a bioadhesive tablet having both controlled and sustained release properties due to a tablet formulation wherein the active ingredient is only progressively made bioavailable over an extended time period by the progressive hydration of the tablet's dry reservoir of active ingredient.

It is another object of the invention to provide a bioadhesive tablet according to the invention that also gelifies and/or swells to help protect a patient using the tablet buccally from asphyxiation, particularly a sleeping patient undergoing treatment.

It is yet another object of the invention to provide methods of making bioadhesive tablets in accordance with the aforementioned objects of the invention. In accordance with one aspect of the invention, there is provided a method of making bioadhesive tablets wherein an active ingredient resistant to premature metabolism and/or degradation is added in the first and/or second step (manufacture of granulate). In accordance with a related aspect of the invention there is provided a method of making bioadhesive tablets wherein an active ingredient prone to premature metabolism and/or degradation is added in the second step (manufacture of the tableting mixture) after the granulate is dried and sieved. Of course, other concerns or factors may affect the choice of which step or steps are appropriate for adding a particular active ingredient.

It is yet another object of the invention to provide methods of using bioadhesive tablets as described herein. In accordance with one aspect of the invention, there is provided a method of using a bioadhesive tablet to administer to a male patient a sustained release of testosterone. In accordance with a related aspect of the invention, there is provided a method of using a bioadhesive tablet to administer to a female patient a sustained release of a hormone, such as testosterone.

The inventors of the present invention have discovered, quite unexpectedly, that these and other objects for the invention may be achieved by making and using tablets comprising an active ingredient, water soluble polymers (e.g., carbomer 974P or 934P, or CARBOPOL™ 974P), and insoluble polycarbophil (e.g., NOVEON®, available from B. F. Goodrich Specialty Polymers of Cleveland, Ohio), and preferably hydroxypropylmethyl cellulose (HPMC), lactose, corn starch and other standard tablets ingredients, such as magnesium stearate, talc, and silica.

Bioadhesive, progressive hydration tablets according to the invention may be used with any suitable active ingredient and may be used to deliver a therapeutic amount of the active ingredient to a patient at controlled rates for sustained periods of time. Tablets according to the invention may also be constructed in any suitable shape and any suitable size consistent with the intended therapeutic use of the tablet.

Tablets according to the invention may comprise any suitable amount of active ingredient. Suitable amounts of active ingredient according to the invention may be from minuscule amounts to about 50%, or more. As will be appreciated by one of ordinary skill in the art, "minuscule amounts" is intended to cover those amounts of active ingredient that are disproportionately small relative to the tablet, for example, when only a few micrograms of active ingredient are to be delivered via a tablet weighing over a hundred milligrams. Accordingly, one of ordinary skill in the art will appreciate that any amount of active ingredient, in any ratio, is within the scope of the present invention.

The balance of the tablet according to the invention may comprise water soluble polymer(s) and water insoluble cross-linked polycarboxylic polymer(s). Also, according to the invention, exemplary tablets preferably have between about 1% and about 75% by weight water soluble polymer (preferably carbomer 974P) and between about 0.5% and about 10% by weight water insoluble, water-swellable cross-linked polycarboxylic polymer (preferably Polycarbophil). In accordance with the invention, such exemplary tablets also preferably include between about 5% and about 50% cellulose. Also in accordance with the invention, presently preferred tablets may have between about 0.5% and about 25% by weight starch. These preferred tablets may also have between about 1% and about 50%, or as much as 95%, by weight lactose.

Furthermore, according to the invention, preferred tablets may comprise from about 0.01% up to about 2% silica; and/or up to about 5% to 8% by weight talc; and/or up to about 2.5% by weight magnesium stearate.

Accordingly, one of ordinary skill in the art will appreciate that the components of the tablets can be varied to suit a particular purpose. For example, the inventors of the present invention have discovered that one way of increasing (decreasing) the time it takes a progressive hydration tablet to hydrate is by increasing (decreasing) the amount of lactose and/or starch and decreasing (increasing) the amount of water-soluble polymer. Alternatively, the density of the tablet may be altered to affect the hydration period.

Active ingredients suitable for use in the present invention include any active ingredient or ingredients requiring sustained or controlled release, any active ingredient or ingredients requiring extended protection from premature degradation by moisture, pH effects, or enzymes, or any active ingredient requiring administration to a patient with protection from first-pass hepatic metabolism. Exemplary active ingredients suitable for use with the present invention include, but are by no means limited to: (1) glycoproteins, such as follicle-stimulating hormone (FSH), luteinizing hormone (LH), human chorionic gonadotropin (HCG), thryoid-stimulating hormone (TSH), and the like; (2) proteins, such as GnRH (agonist and antagonist), oxytocin analogs, somatostatin analogs, tissue plaminogen activator (TPA), growth hormone releasing hormone (GHRH), corticotropin-releasing hormone analogs (CRH analogs), and the like; (3) sex hormones, such as estradiol, testosterone, progesterone, and the like; (4) anti-hormones, such as tamoxifen, mifepristone, and the like; (5) nitrates, such as nitroglycerin, isosorbide, erythrityl tetranitrate, pentaerythritol tetranitrate, and the like; (6) beta-agonists, such as terbutaline, albuterol, pirbuterol, bitolterol, ritodrine, and the like; (7) beta-antagonists, such as propranolol, metoprolol, nadolol, atenolol, timolol, esmolol, pindolol, acebutolol, labetalol, and the like; (8) opioids, such as morphine, hydromorphone, oxymorphone, codeine, hydrocodone, oxycodone, leverophanol, levallorphan, buprenorphine, fentanyl, nalbuphine, butorphanol, pentazocine, and the like; (9) opioids-antagonists, such as naloxone, nalmefene, and the like; (10) antidepressants, such as amitriptyline, amoxapine, desipramine, doxepin, imipramine, maprotilen, nortriptyline, protripyline, trimipramine, fluoxetine, trazodone, and the like; (11) HMG CoA reductase inhibitors, such as lovastatin, mevastatin, simvastatin, pravastatin, atorvastatin, and the like; (12) antihistamines, such as loratadine, chlorpheniramine maleate, brompheniramine maleate, diphenhydramine, dimenhydrinate, carbinoxamine, promethazine, tripelannamine, and the like; (13) ACE inhibitors, such as captopril, enalapril, lisinopril, and the like; and, (14) prostaglandins, such as misoprostol and the like. Accordingly, one of ordinary skill in the art will appreciate that tablets according to the invention may be used with a wide variety of active ingredients to treat a wide variety of conditions.

The present invention also provides a pharmaceutical composition comprising an effective amount of active ingredient that is metabolized by 5α-reductase, a water insoluble, water-swellable cross-linked polycarboxylic polymer, and a water soluble polymer, wherein said composition is formulated to deliver said active ingredient to the bloodstream of a mammal through a mucosal surface of the mammal.

The present invention further provides a method of delivering to a mammal an active ingredient that is metabolized by 5α-reductase, comprising administering said active ingredient via a progressive hydration bioadhesive composition through a mucosal surface of the mammal.

In addition, the present invention provides a composition for delivering to the bloodstream of a mammal an active ingredient that is metabolized by 5α-reductase, comprising a water insoluble cross-linked polycarboxylic polymer, and a water soluble polymer, wherein said composition is formulated to deliver said active ingredient through a mucosal surface of the mammal.

In addition, the present invention provides a bioadhesive progressive hydration pharmaceutical composition comprising: an effective amount of testosterone, a water insoluble, water-swellable cross-linked polycarboxylic polymer, and a water soluble polymer, wherein said composition is formulated to deliver said testosterone to the bloodstream of a mammal through a mucosal surface of the mammal.

In addition, the present invention provides a bioadhesive progressive hydration pharmaceutical composition comprising an effective amount of terbutaline, a water insoluble, water-swellable cross-linked polycarboxylic polymer, and a water soluble polymer, wherein said composition is formulated to deliver said terbutaline to the bloodstream of a mammal through a mucosal surface of the mammal.

In addition, the present invention provides a method of delivering to a mammal an effective amount of testosterone via a progressive hydration bioadhesive pharmaceutical composition through a mucosal surface of the mammal, comprising said testosterone, a water insoluble, water-swellable cross-linked polycarboxylic polymer, and a water soluble polymer.

In addition, the present invention provides a method of delivering to a mammal an effective amount of terbutaline via a progressive hydration bioadhesive pharmaceutical composition through a mucosal surface of the mammal, comprising said terbutaline, a water insoluble, water-swellable cross-linked polycarboxylic polymer, and a water soluble polymer.

Preferably, the compositions of the present invention are formulated to deliver said active ingredient via the mammal's vaginal, buccal, nasal or rectal cavity.

The aforementioned and other aspects of the invention will become more clear by reference to the Figures and descriptions of preferred embodiments.

A preferred embodiment of the invention is depicted in FIG. 1. As shown in the first-frame of FIG. 1, before the tablet is administered all of the active is in the dry state and thus, not subject to the deleterious action of moisture, pH effects, enzymes or other chemicals. It is also not available for absorption (bioavailable). As shown in frames 2–6 of FIG. 1, over time the residual portion of the active remains in the dry state which both protects it from water and the immediate environment as well as allowing it to serve as a reservoir for the sustained and controlled release of the active. Such a delivery system is well suited for the delivery of proteins, glycoproteins, and other drugs which must be protected from metabolism or during prolonged administration from enzymatic, pH, or moisture-induced degradation.

In a preferred embodiment, when used buccally, progressive hydration of the bioadhesive tablet protects the patient, should the tablet become dislodged, by gelifying and becoming heavier and thus less likely to float in the airway, risking aspiration. This makes this embodiment particularly well suited for agents that should reach their peak levels in the middle of the night, e.g., hormones like testosterone or steroids to treat asthma. According to the invention, the hydration of the tablet can preferably take hours (e.g. 12 to 24 hours) when formulated for buccal tablets or even days when formulated for vaginal use. As will be appreciated by one of ordinary skill in the art, prior art bioadhesive tablets do not protect the active ingredient from moisture, pH, or from enzymes produced by bacteria in the septic oral and vaginal orifices.

Furthermore, as will be appreciated by one of ordinary skill in the art following the teaching of the present application, the tablet can be sized, shaped and dosed to meet the needs of the particular treatment being undertaken. For example, the buccal bioadhesive tablet depicted in FIG. 1 was constructed to be only 9 mm in diameter for the comfort of the patient, but made capable of delivering 7 mg of testosterone per day, full physiologic level. By contrast, prior art transdermal patches were only capable of delivering 5 mg per day, in other words a sub-physiologic level.

Figure 2:
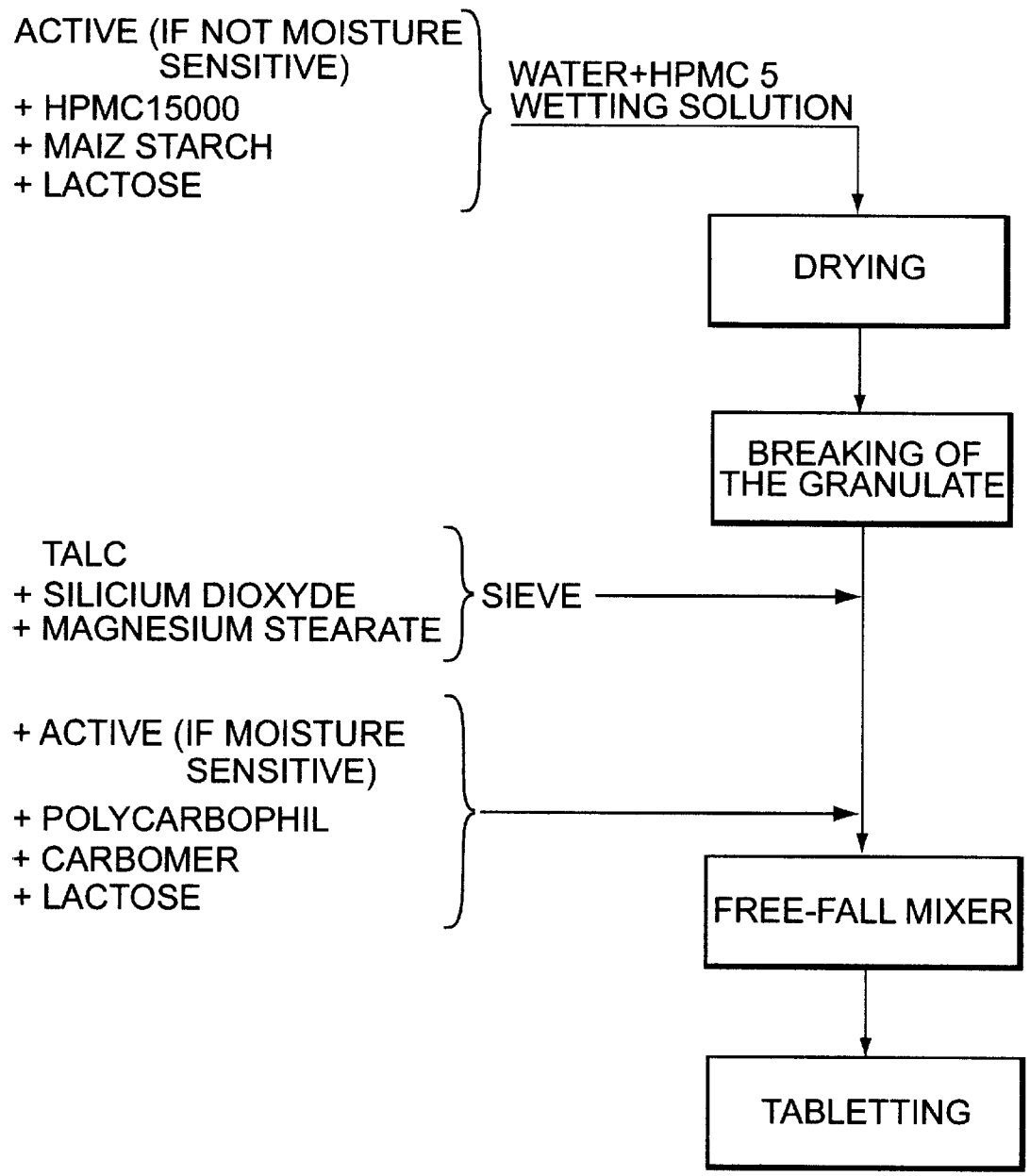
FIG. 2 is a flowchart depicting a presently preferred method of making bioadhesive tablets according to the invention.

A presently preferred method of manufacturing bioadhesive tablets is diagramed in FIG. 2. The presently preferred method involves three steps as described below:

1. First step: manufacture of the granulate.

Hydroxypropylmethyl cellulose 15000(=HPMC 15000) is mixed with corn starch and lactose and in case of an active ingredient not sensitive to moisture the active is added. The mixture is wet with an aqueous solution of hydroxypropylmethyl cellulose 5 (=HPMC 5) and knead/granulated.

The granulate is dried in an oven under warm air (50° C.) until moisture content is less than 2.5%.

The dried granulate is broken with a stainless steel sieve oscillating granulator mesh size 1000 μm.

2. Second step: the tableting mixture.

Talc, silicon dioxide magnesium stearate, and in a case of an active ingredient sensitive to moisture, the active ingredient is added. All is sieved through a sieving machine having aperture size 500 μm and then transferred into a free-fall mixer.

Addition of the granulate of step 1, followed by polycarbophil, carbomer and lactose. The whole is mixed until homogenous.

3. Third step: tableting.

The tableting mixture is compressed into tablets by means of a rotative tableting machine equipped with punches 9 mm flat on the upper side and curved (r=9 mm) on the lower side both with beveled edge. The tablets are dedusted and packed.

As depicted in FIG. 2, an active ingredient that is not sensitive to moisture is preferably added during the manufacture of the granulate. However, alternatively, the active ingredient can be added during the second step after the granulate is dried and sieved. Also, as will be appreciated by one of ordinary skill in the art, this second method is particularly preferred when the active ingredient is sensitive to moisture.

In a presently preferred manufacturing process, the active ingredient is preferably protected from moisture. A wet granulation is made of lactose, corn starch and HPMC. Testosterone, polycarbophil, carbomer 974P, talc and magnesium stearate are added dry for the final compression.

Furthermore, as will be appreciated by one of ordinary skill in the art following the teaching of the present application, the materials of construction can be varied to optimize the desired characteristics of the tablet. For example, the present inventors have discovered that by progressively increasing the amount of lactose and corn starch and progressively decreasing the amount of carbomer 974P, the amount of time it takes a tablet to hydrate is progressively increased. Accordingly, as will be appreciated by one of ordinary skill in the art, tablets suited for specific treatments (i.e., specific active, specific dose, specific delivery time) can be manufactured.

These and other aspects of the invention may be more clearly shown by way of example.

EXAMPLE 1

Testosterone Tablet

The following is an example of a formulation (Formulation 8, batch #00029906) designed for complete physiologic replacement of testosterone in men:

| INGREDIENT | AMOUNT | % w/w |
| --- | --- | --- |
| Testosterone | 30.000 mg | 24.0% |
| HPMC | 26.250 mg | 21.0% |
| Corn Starch | 22.500 mg | 18.0% |
| Monohydrated Lactose | 30.125 mg | 24.1% |
| Silica | 1.250 mg | 1.0% |

-continued

| INGREDIENT | AMOUNT | % w/w |
|---|---|---|
| Polycarbophil (Noveon) | 3.125 mg | 2.5% |
| Carbomer 974P | 9.375 mg | 7.5% |
| Talc | 1.500 mg | 1.2% |
| Magnesium stearate | 0.875 mg | 0.7% |

Formulations like the one above produced sustained release in in-vitro dissolution tests. When used in female subjects formulas like this one also produce a sustained and controlled release of testosterone for 12 hours or more.

Formulations like the one above also provide a blood serum concentration ratio of testosterone to 5α-dihydrotestosterone (DHT) of about 12 to 1 in the bloodstream of said mammal. It is contemplated that this serum concentration ratio preferably is about 10 to 1 or greater.

The individual ingredients are well known and readily available from suppliers known in the industry.

HPMC, or hydroxypropylmethylcellulose, is a swelling, dispersing agent. Alternates, which are well-known in the industry, include other water-swellable forms of cellulose and polymers.

Corn (maize) starch is a filler and binder. Alternates are well-known in the industry.

Lactose is a filler. Alternatives are well-known in the industry.

Silica, or silicon dioxide (silicium dioxyde), acts as a suspending and thickening agent. Alternatives are well-known in the industry.

Talc and magnesium stearate are lubricant powders commonly used in the manufacture of compressed tablets. Alternatives are well-known in the industry.

Carbomer 934P or 974P (or CARBOPOL™ 974P) is the water soluble polymer. This polymer provides the initial bioadhesion. Alternatives are well-known in the industry, and include, for example, other water-soluble polymers.

Polycarbophil is the water insoluble polymer, and provides the extended bioadhesion. Alternatives would include, for example, other water-insoluble, water-swellable bioadhesive polymers.

Table 1 depicts nine different formulations of bioadhesive tablets according to the invention. The active ingredient, testosterone, was held constant at 30.0 mg (24% by weight) so the effect of varying the proportions of the inactive ingredients could be studied.

The testosterone dissolution rates of selected formulations were then studied. Table 2 depicts the testosterone dissolution rate of six tablets selected from Formula 1, batch #0069904. Table 3 depicts the testosterone dissolution rate of six tablets selected from Formula 3, batch #0049904. Table 4 depicts the testosterone dissolution rate of six tablets selected from Formula 5, batch #0029904. Table 5 depicts the testosterone dissolution rate of Formula 6, batch #0019904.

Figure 3:
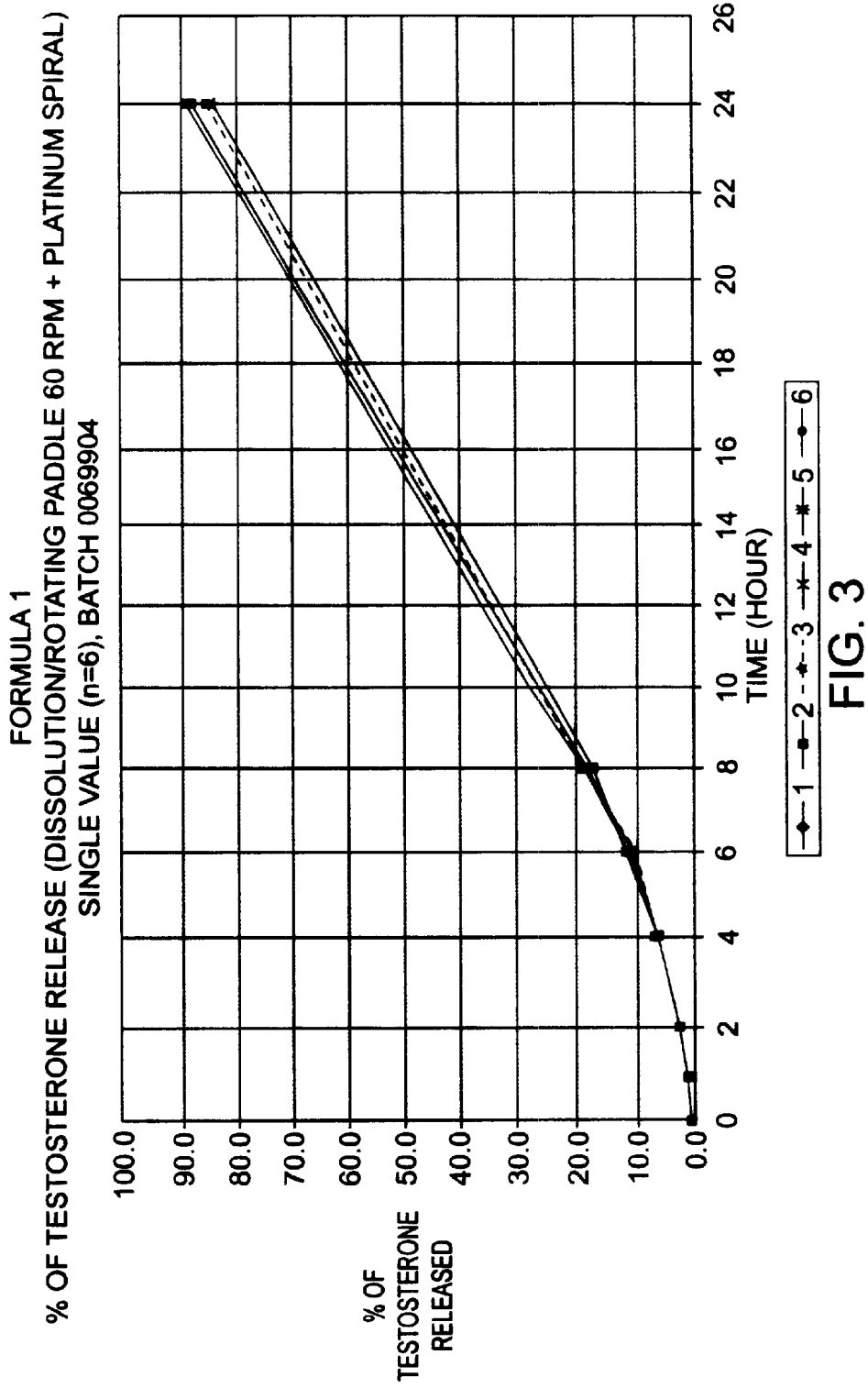
Figure 4:
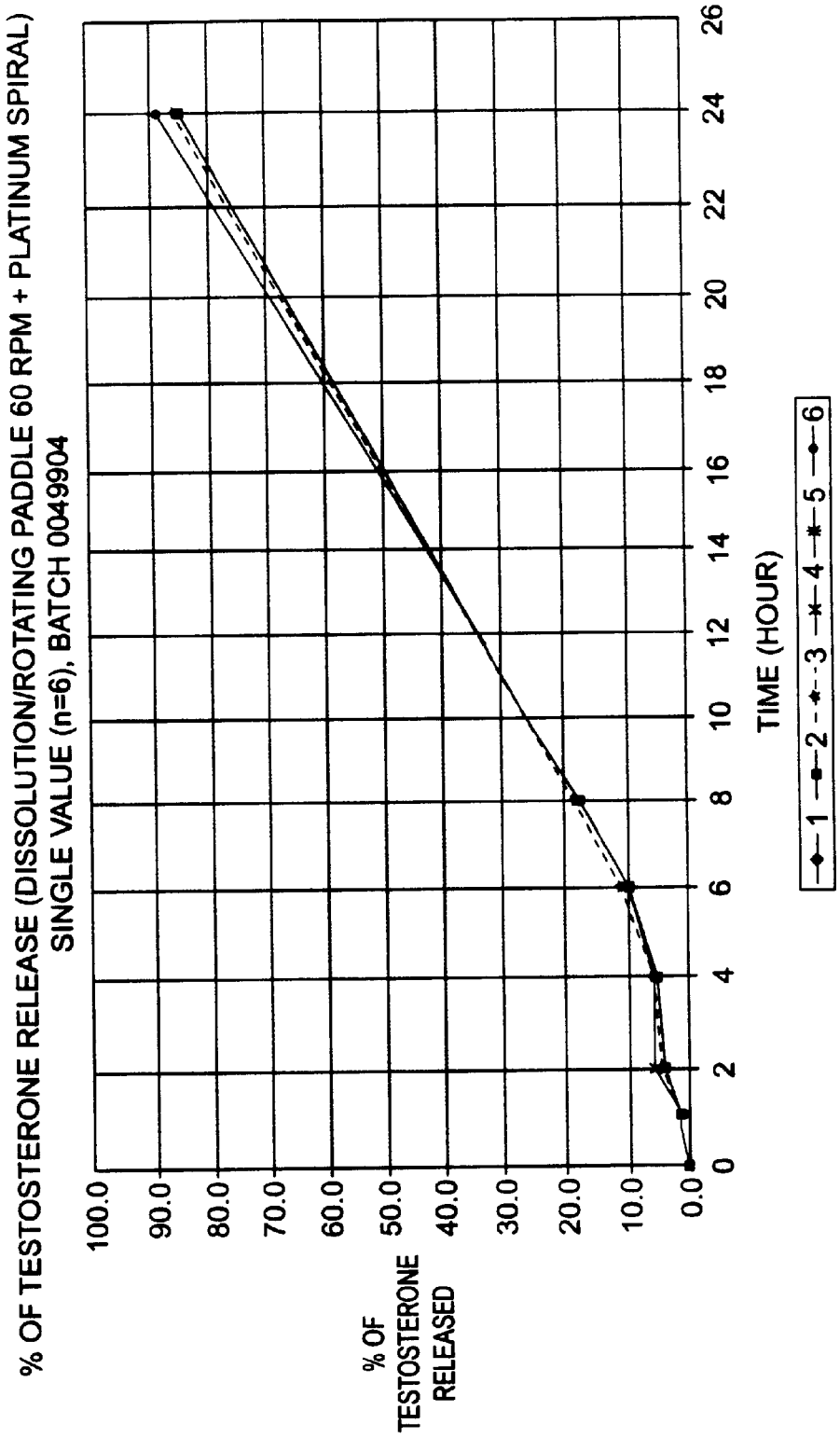
Figure 5:
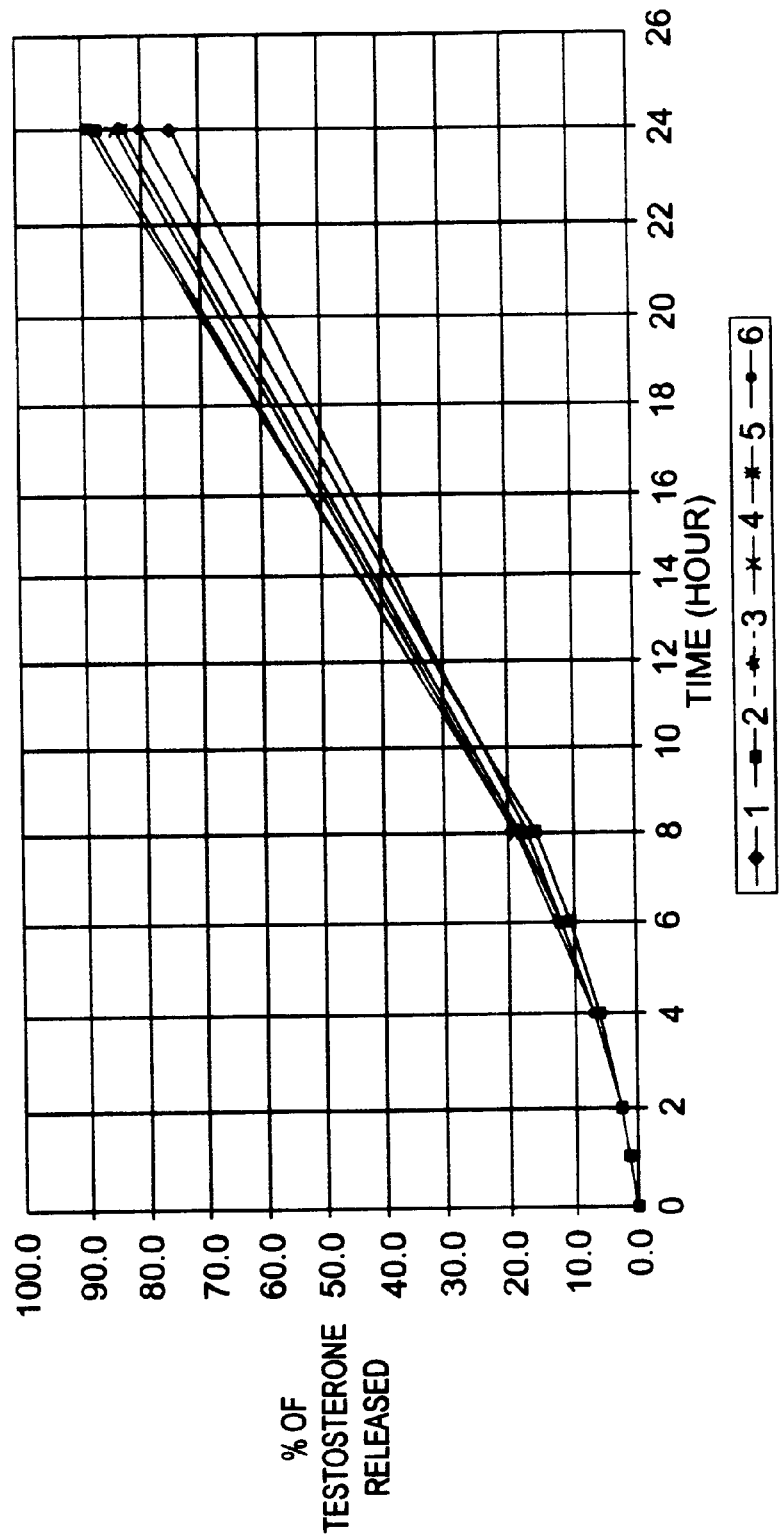

The dissolution rate data was then graphed to illustrate the percent of testosterone released per hour. FIG. 3 (Chart 1) depicts the testosterone release rate for Formula 1 (see Table 2). FIG. 4 (Chart 2) depicts the testosterone release rate for Formula 3 (see Table 3). FIG. 5 (Chart 3) depicts the testosterone release rate for Formula 5 (see Table 4). FIG. 6 (Chart 4) depicts the testosterone release rate for Formula 6 (see Table 5).

TABLE 1

Testosterone KT

| | Form. 1 0069904 | | Form. 2 0059904 | | Form. 3 0049904 | | Form. 4 0039904 | |
|---|---|---|---|---|---|---|---|---|
| Batch # | mg | % by Weight | mg | % by Weight | mg | % by Weight | mg | % by Weight |
| Testosterone | 30.000 | 24.00 | 30.000 | 24.00 | 30.000 | 24.00 | 30.000 | 24.00 |
| HPMC* 90SH-15000 | 31.250 | 25.00 | 30.000 | 24.00 | 28.750 | 23.00 | 27.500 | 22.00 |
| Cornstarch | 2.500 | 2.00 | 7.500 | 6.00 | 12.500 | 10.00 | 17.500 | 14.00 |
| Monohydrated lactose | 11.375 | 9.10 | 13.875 | 11.10 | 16.375 | 13.10 | 18.875 | 15.10 |
| Silica | 1.250 | 1.00 | 1.250 | 1.00 | 1.250 | 1.00 | 1.250 | 1.00 |
| Polycarbophil acid (Noveon AA-) | 3.125 | 2.50 | 3.125 | 2.50 | 3.125 | 2.50 | 3.125 | 2.50 |
| Carbomer 974 P | 43.750 | 35.00 | 37.500 | 30.00 | 31.250 | 25.00 | 25.000 | 20.00 |
| Talc | 0.875 | 0.70 | 0.875 | 0.70 | 0.875 | 0.70 | 0.875 | 0.70 |
| Magnesium sterate | 0.875 | 0.70 | 0.875 | 0.70 | 0.875 | 0.70 | 0.875 | 0.70 |
| Total Weight | 125.000 | 100.00 | 125.000 | 100.00 | 125.000 | 100.00 | 125.000 | 100.00 |

| | Form. 5 0029904 | | Form. 6 0019904 | | Form. 7 00019906 | | Form. 8 00029906 | | Form. 9 00039906 | |
|---|---|---|---|---|---|---|---|---|---|---|
| Batch # | mg | % by Weight | mg | % by Weight | mg | % by Weight | mg | % by Weight | mg | % by Weight |
| Testosterone | 30.000 | 24.00 | 30.000 | 24.00 | 30.000 | 24.00 | 30.000 | 24.00 | 30.000 | 24.00 |
| HPMC* 90SH-15000 | 26.250 | 21.00 | 26.250 | 21.00 | 26.250 | 21.00 | 26.250 | 21.00 | 26.250 | 21.00 |
| Cornstarch | 22.500 | 18.00 | 22.500 | 18.00 | 22.500 | 18.00 | 22.500 | 18.00 | 22.500 | 18.00 |
| Monohydrated lactose | 21.375 | 17.10 | 24.500 | 19.60 | 27.625 | 22.10 | 30.125 | 24.10 | 33.250 | 26.60 |
| Silica | 1.250 | 1.00 | 1.250 | 1.00 | 1.250 | 1.00 | 1.250 | 1.00 | 1.250 | 1.00 |

TABLE 1-continued

| Testosterone KT | | | | | | | | | | |
|---|---|---|---|---|---|---|---|---|---|---|
| Polycarbophil acid (Noveon AA-) | 3.125 | 2.50 | 3.125 | 2.50 | 3.125 | 2.50 | 3.125 | 2.50 | 3.125 | 2.50 |
| Carbomer 974 P | 18.750 | 15.00 | 15.625 | 12.50 | 12.500 | 10.00 | 9.375 | 7.50 | 6.250 | 5.00 |
| Talc | 0.875 | 0.70 | 0.875 | 0.70 | 0.875 | 0.70 | 1.500 | 1.20 | 1.500 | 1.20 |
| Magnesium sterate | 0.875 | 0.70 | 0.875 | 0.70 | 0.875 | 0.70 | 0.875 | 0.70 | 0.875 | 0.70 |
| Total Weight | 125.000 | 100.00 | 125.000 | 100.00 | 125.000 | 100.00 | 125.000 | 100.00 | 125.000 | 100.00 |

*Hydroxypropylmethyl cellulose

TABLE 2

TESTOSTERONE DISSOLUTION RATE - PERCENT DISSOLUTION
BATCH: 0069904 (Formula 1)
DISSOLUTION APPARATUS: ROTATING PADDLE 60 RPM/PLATINUM WIRE SPIRAL

| SAMPLE | WITHDRAW (HOUR) 0 | WITHDRAW (HOUR) 1 | WITHDRAW (HOUR) 2 | WITHDRAW (HOUR) 4 | WITHDRAW (HOUR) 6 | WITHDRAW (HOUR) 8 | WITHDRAW (HOUR) 24 |
|---|---|---|---|---|---|---|---|
| 1 | 0.0 | 0.7 | 1.9 | 7.6 | 10.6 | 16.0 | 83.6 |
| 2 | 0.0 | 0.6 | 1.7 | 6.7 | 11.7 | 18.0 | 88.5 |
| 3 | 0.0 | 0.7 | 2.0 | 6.9 | 11.7 | 17.9 | 84.9 |
| 4 | 0.0 | 0.6 | 1.7 | 7.0 | 11.2 | 17.1 | 88.3 |
| 5 | 0.0 | 0.7 | 1.9 | 6.8 | 10.9 | 17.0 | 87.4 |
| 6 | 0.0 | 0.7 | 2.1 | 6.6 | 12.4 | 18.3 | 86.6 |
| AVERAGE VALUE | 0.0 | 0.7 | 1.9 | 6.9 | 11.4 | 17.4 | 86.6 |

TABLE 3

TESTOSTERONE DISSOLUTION RATE - PERCENT DISSOLUTION
BATCH: 0049904 (Formula 3)
DISSOLUTION APPARATUS: ROTATING PADDLE 60 RPM/PLATINUM WIRE SPIRAL

| SAMPLE | WITHDRAW (HOUR) 0 | WITHDRAW (HOUR) 1 | WITHDRAW (HOUR) 2 | WITHDRAW (HOUR) 4 | WITHDRAW (HOUR) 6 | WITHDRAW (HOUR) 8 | WITHDRAW (HOUR) 24 |
|---|---|---|---|---|---|---|---|
| 1 | 0.0 | 0.9 | 3.1 | 5.6 | 10.6 | 16.5 | 83.6 |
| 2 | 0.0 | 1.1 | 3.1 | 5.6 | 10.5 | 16.9 | 82.2 |
| 3 | 0.0 | 1.2 | 3.4 | 6.3 | 11.8 | 18.0 | 83.4 |
| 4 | 0.0 | 0.9 | 2.9 | 5.4 | 10.8 | 16.7 | 82.7 |
| 5 | 0.0 | 1.1 | 4.9 | 5.7 | 10.6 | 16.7 | 83.0 |
| 6 | 0.0 | 1.0 | 2.9 | 5.6 | 11.0 | 16.8 | 85.6 |
| AVERAGE VALUE | 0.0 | 1.0 | 3.4 | 5.7 | 10.9 | 16.9 | 83.4 |

TABLE 4

TESTOSTERONE DISSOLUTION RATE - PERCENT DISSOLUTION
BATCH: 0029904 (Formula 5)
DISSOLUTION APPARATUS: ROTATING PADDLE 60 RPM/PLATINUM WIRE SPIRAL

| SAMPLE | WITHDRAW (HOUR) 0 | WITHDRAW (HOUR) 1 | WITHDRAW (HOUR) 2 | WITHDRAW (HOUR) 4 | WITHDRAW (HOUR) 6 | WITHDRAW (HOUR) 8 | WITHDRAW (HOUR) 24 |
|---|---|---|---|---|---|---|---|
| 1 | 0.0 | 0.9 | 2.2 | 5.9 | 10.8 | 16.3 | 80.3 |
| 2 | 0.0 | 0.9 | 2.5 | 6.7 | 11.8 | 17.8 | 87.5 |
| 3 | 0.0 | 0.9 | 2.4 | 6.9 | 12.3 | 17.7 | 75.2 |
| 4 | 0.0 | 0.9 | 2.3 | 6.8 | 12.4 | 18.6 | 82.4 |
| 5 | 0.0 | 0.9 | 2.5 | 6.9 | 12.9 | 19.5 | 83.2 |
| 6 | 0.0 | 0.9 | 2.2 | 6.6 | 12.2 | 18.8 | 86.6 |
| AVERAGE VALUE | 0.0 | 0.9 | 2.4 | 6.6 | 12.1 | 18.1 | 82.5 |

TABLE 5

TESTOSTERONE DISSOLUTION RATE - PERCENT DISSOLUTION
BATCH: 0019904 (Formula 6)
DISSOLUTION APPARATUS: ROTATING PADDLE 60 RPM/PLATINUM WIRE SPIRAL

| SAMPLE | WITHDRAW (HOUR) 0 | WITHDRAW (HOUR) 1 | WITHDRAW (HOUR) 2 | WITHDRAW (HOUR) 4 | WITHDRAW (HOUR) 6 | WITHDRAW (HOUR) 8 | WITHDRAW (HOUR) 24 |
|---|---|---|---|---|---|---|---|
| 1 | 0.0 | 1.2 | 2.1 | 5.9 | 11.1 | 16.1 | 71.7 |
| 2 | 0.0 | 0.8 | 2.0 | 5.0 | 9.7 | 14.1 | 70.1 |
| 3 | 0.0 | 0.9 | 2.3 | 6.4 | 11.3 | 15.8 | 74.6 |
| 4 | 0.0 | 0.9 | 2.0 | 5.5 | 10.4 | 15.0 | 68.6 |
| 5 | 0.0 | 0.8 | 1.8 | 4.9 | 9.9 | 14.6 | 76.6 |
| 6 | 0.0 | 0.9 | 1.8 | 4.9 | 9.1 | 13.1 | 70.3 |
| AVERAGE VALUE | 0.0 | 0.9 | 2.0 | 5.4 | 10.3 | 14.8 | 72.0 |

As shown in the charts and tables, by decreasing the amount of lactose and corn starch and increasing the amount of carbomer 974P, the time it takes for the tablet to hydrate is progressively decreased. Formulation 1 (0069904) and others like it with high levels of carbomer 974P and low levels of lactose and corn starch are probably best suited to buccal administration where 12 hours of delivery is usually sufficient. In the first example given above Formulation 8 (0029906), where the levels of lactose and corn starch are high and carbomer 974P is low, the formula is probably better suited for vaginal administration where release is often required over a period of days.

EXAMPLE 2

Testosterone Tablet 30 mg

The following is an example of a formulation designed for testosterone replacement therapy:

| INGREDIENT | AMOUNT/tablet | % w/w |
|---|---|---|
| Testosterone | 30.000 mg | 21.4% |
| HPMC | 26.250 mg | 18.8% |
| Corn Starch | 22.500 mg | 16.1% |
| Lactose | 45.125 mg | 32.2% |
| Silica | 1.250 mg | 0.9% |
| Polycarbophil (Noveon) | 3.125 mg | 2.2% |
| Carbomer 974P | 9.375 mg | 6.7% |
| Talc | 1.500 mg | 1.1% |
| Magnesium stearate | 0.875 mg | 0.6% |

EXAMPLE 3

Testosterone Tablet (6 mg)

The following is an example of a formulation designed for testosterone replacement therapy:

| INGREDIENT | AMOUNT/tablet | % w/w |
|---|---|---|
| Testosterone | 6.000 mg | 6.0% |
| HPMC | 5.250 mg | 5.3% |
| Corn Starch | 4.500 mg | 4.5% |
| Lactose | 78.970 mg | 79.0% |
| Silica | 0.700 mg | 0.7% |
| Polycarbophil (Noveon) | 2.230 mg | 2.2% |
| Carbomer 974P | 1.000 mg | 1.0% |
| Talc | 0.850 mg | 0.9% |
| Magnesium stearate | 0.500 mg | 0.5% |

EXAMPLE 4

Testosterone Tablet (3 mg)

The following is an example of a formulation designed for testosterone replacement therapy:

| INGREDIENT | AMOUNT/tablet | % w/w |
|---|---|---|
| Testosterone | 3.000 mg | 3.0% |
| HPMC | 2.625 mg | 2.6% |
| Corn Starch | 2.250 mg | 2.3% |
| Lactose | 86.845 mg | 86.8% |
| Silica | 0.700 mg | 0.7% |
| Polycarbophil (Noveon) | 2.230 mg | 2.2% |
| Carbomer 974P | 1.000 mg | 1.0% |
| Talc | 0.850 mg | 0.9% |
| Magnesium stearate | 0.500 mg | 0.5% |

EXAMPLE 5

Terbutaline Tablet (4 MG)

The following is an example of a terbutaline formulation designed to provide certain therapeutic benefits of terbutaline administration:

| INGREDIENT | AMOUNT/tablet | % w/w |
|---|---|---|
| Terbutaline sulfate | 4.000 mg | 4.4% |
| HPMC | 18.760 mg | 20.8% |
| Corn Starch | 16.070 mg | 17.9% |
| Lactose | 39.640 mg | 44.0% |
| Silica | 0.900 mg | 1.0% |
| Polycarbophil (Noveon) | 2.235 mg | 2.5% |
| Carbomer 974P | 6.700 mg | 7.4% |
| Talc | 1.070 mg | 1.2% |
| Magnesium stearate | 0.625 mg | 0.7% |

EXAMPLE 6

Terbutaline Tablet (2 MG)

The following is an example of a terbutaline formulation designed to provide certain therapeutic benefits of terbutaline administration:

| INGREDIENT | AMOUNT/tablet | % w/w |
|---|---|---|
| Terbutaline Sulfate | 2.000 mg | 2.2% |
| HPMC | 18.760 mg | 20.8% |
| Corn Starch | 16.070 mg | 17.9% |
| Lactose | 41.640 mg | 46.3% |
| Silica | 0.900 mg | 1.0% |
| Polycarbophil (Noveon) | 2.235 mg | 2.5% |
| Carbomer 974P | 6.700 mg | 7.4% |
| Talc | 1.070 mg | 1.2% |
| Magnesium stearate | 0.625 mg | 0.7% |

As will be appreciated by one of ordinary skill in the art, the examples and preferred embodiments are not intended to be limiting, and the invention applies to tablets comprised of any active ingredient and any combination of tablet materials. Furthermore, as will be appreciated by one of ordinary skill in the art, the invention is intended to cover the methods of manufacturing and therapeutic uses of the aforementioned tablets.

The invention being thus described, it will be apparent to those skilled in the art that the same may be varied in many ways without departing from the spirit and scope of the invention. Such variations are included within the scope of the appended claims.

All publications and patents or applications mentioned in this specification are herein incorporated by reference to the same extent as if each was specifically and individually indicated to be incorporated by reference.

We claim:

1. A bioadhesive, controlled and sustained release, progressive hydration pharmaceutical composition comprising:
    an effective amount of terbutaline,
    a water insoluble, water-swellable cross-linked polycarboxylic polymer, and
    a water soluble polymer,
    wherein said composition is formulated to deliver said terbutaline to the bloodstream of a mammal through a mucosal surface of the mammal.

2. The composition of claim 1, wherein said terbutaline is present in an amount of about 4 mg/per unit dosage of composition.

3. The composition of claim 1, wherein said terbutaline is present in an amount of about 2 mg/per unit dosage of composition.

4. The composition of claim 1, wherein
    the mucosal surface is the vagina,
    and said water insoluble, water-swellable cross-linked polycarboxylic polymer is Polycarbophil.

5. The composition of claim 2, wherein
    the mucosal surface is the vagina,
    and said water insoluble, water-swellable cross-linked polycarboxylic polymer is Polycarbophil.

6. The composition of claim 3, wherein
    the mucosal surface is the vagina,
    and said water insoluble, water-swellable cross-linked polycarboxlic polymer is Polycarbophil.

7. The composition of any one of claims 4, 5, or 6, wherein
    said water soluble polymer is carbomer 974P,
    and said composition further comprises lactose, hydroxypropylmethylcellulose, corn starch, talc, silica, and magnesium stearate.

8. A method of delivering to a mammal an effective amount of terbutaline via a controlled and sustained release, progressive hydration bioadhesive pharmaceutical composition through a mucosal surface of the mammal, comprising
    said terbutaline,
    a water insoluble, water-swellable cross-linked polycarboxylic polymer, and
    a water soluble polymer.

9. The method of claim 8, wherein said terbutaline is present in an amount of about 4 mg/per unit dosage of said composition.

10. The method of claim 8, wherein said terbutaline is present in an amount of about 2 mg/per unit dosage of composition.

11. The method of claim 8, wherein
    the mucosal surface is the vagina,
    said water insoluble, water-swellable cross-linked polycarboxylic polymer is polycarbophil,
    said water soluble polymer is carbomer 974P,
    and said composition further comprises lactose, hydroxypropylmethylcellulose, corn starch, talc, silica, and magnesium stearate.

12. The method of claim 9, wherein
    the mucosal surface is the vagina,
    said water insoluble, water-swellable cross-linked polycarboxylic polymer is polycarbophil,
    said water soluble polymer is carbomer 974P,
    and said composition further comprises lactose, hydroxypropylmethylcellulose, corn starch, talc, silica, and magnesium stearate.

13. The method of claim 10, wherein
    the mucosal surface is the vagina,
    said water insoluble, water-swellable cross-linked polycarboxylic polymer is polycarbophil,
    said water soluble polymer is carbomer 974P,
    and said composition further comprises lactose, hydroxypropylmethylcellulose, corn starch, talc, silica, and magnesium stearate.

* * * * *

UNITED STATES PATENT AND TRADEMARK OFFICE
CERTIFICATE OF CORRECTION

PATENT NO.     : 6,624,200 B2
DATED          : September 23, 2003
INVENTOR(S)    : Bologna et al.

It is certified that error appears in the above-identified patent and that said Letters Patent is hereby corrected as shown below:

Title page,
Item [63], Related U.S. Application Data, delete "08/379,310" and insert
-- 09/379,310 --.

Column 5,
Line 68, delete "thryoid-" and insert -- thyroid- --.

Columns 9-10,
TABLE 1, under the heading "Batch #", after "Magnesium", delete "sterate" and insert
-- stearate --.

Columns 11-12,
TABLE 1-continued, after "Magnesium", insert -- stearate --; and before "Total
Weight" delete "sterate".

Column 13,
Line 34, after "Testosterone Tablet", delete "30 mg" and insert -- (30 mg) --.

Column 16,
Line 14, delete "bioadbesive" and insert -- bioadhesive --; and
Line 25, after "2 mg/per unit dosage of", insert -- said --.

Signed and Sealed this

Second Day of March, 2004

JON W. DUDAS
*Acting Director of the United States Patent and Trademark Office*